(12) United States Patent
Zhang et al.

(10) Patent No.: US 10,578,530 B2
(45) Date of Patent: Mar. 3, 2020

(54) EXPERIMENTAL METHOD FOR INDOOR REAL-TIME DYNAMIC MONITORING OF HYDRAULIC FRACTURE WIDTH

(71) Applicant: China University of Petroleum-Beijing, Beijing (CN)

(72) Inventors: Guangqing Zhang, Beijing (CN); Ying Lin, Beijing (CN); Xiao Yang, Beijing (CN); Yuanyuan Wang, Beijing (CN)

(73) Assignee: China University of Petroleum-Beijing, Beijing (CN)

( * ) Notice: Subject to any disclaimer, the term of this patent is extended or adjusted under 35 U.S.C. 154(b) by 0 days.

(21) Appl. No.: 15/989,712

(22) Filed: May 25, 2018

(65) Prior Publication Data

US 2018/0340873 A1 Nov. 29, 2018

(30) Foreign Application Priority Data

May 27, 2017 (CN) .......................... 2017 1 0391622

(51) Int. Cl.
*G01N 3/00* (2006.01)
*G01N 3/10* (2006.01)
*G01N 33/24* (2006.01)

(52) U.S. Cl.
CPC ................ *G01N 3/10* (2013.01); *G01N 3/00* (2013.01); *G01N 33/24* (2013.01);
(Continued)

(58) Field of Classification Search
CPC ............ G01N 3/10; G01N 3/00; G01N 33/24; G01N 2203/0048; G01N 2203/0067; G01N 2203/0298; G01N 2203/0641
(Continued)

(56) References Cited

U.S. PATENT DOCUMENTS 7,380,466 B2 * 6/2008 Deeg ..................... G01N 33/383
73/803
8,794,078 B2 * 8/2014 Darbe ...................... G01N 3/10
73/803
(Continued)

FOREIGN PATENT DOCUMENTS

CN 203869957 U 10/2014
CN 104154874 A 11/2014
(Continued)

OTHER PUBLICATIONS

CN First Office Action and Search Report dated Feb. 27, 2019, Application No. 201710391622.5.
(Continued)

*Primary Examiner* — Max H Noori
(74) *Attorney, Agent, or Firm* — Young Basile Hanlon & MacFarlane, P.C.

(57) ABSTRACT

An experimental method for indoor real-time dynamic monitoring of a hydraulic fracture width, comprising the steps of: test piece preparation: assembling a prefabricating mold and fixing a fiber grating therein; mounting a simulated wellbore in the prefabricating mold, pouring agitated cement mortar into the prefabricating mold, and the cement mortar is solidified to form a test piece; mounting the test piece into a confining pressure chamber of a true triaxial hydraulic fracturing simulation device, connecting a liquid injection line to the true triaxial hydraulic fracturing simulation device, and connecting the fiber grating to a modem that is connected to a computer; hydraulic fracture width monitoring test: injecting liquid into the confining pressure chamber of the true triaxial hydraulic fracturing simulation device through the liquid injection line to apply three-direction confining pressures to the test piece, injecting liquid into the simulated wellbore, and starting the fiber grating and the modem to dynamically monitor the hydraulic fracture width in the test piece; and when a hydraulic fracture inside the test piece reaches an outer surface of the test piece, ending the test.

12 Claims, 4 Drawing Sheets

(52) U.S. Cl.
CPC ............... *G01N 2203/0048* (2013.01); *G01N 2203/0067* (2013.01); *G01N 2203/0298* (2013.01); *G01N 2203/0641* (2013.01)

(58) Field of Classification Search
USPC ......................................................... 73/800
See application file for complete search history.

(56) References Cited

U.S. PATENT DOCUMENTS

| | | | | |
|---|---|---|---|---|
| 9,459,245 | B2 * | 10/2016 | Bois ..................... | G01N 33/383 |
| 2009/0217739 | A1 * | 9/2009 | Hardesty .............. | G01N 33/227 |
| | | | | 73/35.17 |

FOREIGN PATENT DOCUMENTS

| | | |
|---|---|---|
| CN | 105403161 A | 3/2016 |
| CN | 105547178 A | 5/2016 |
| CN | 106197342 A | 12/2016 |
| CN | 106321069 A | 1/2017 |

OTHER PUBLICATIONS

CN Second Office Action dated May 13, 2019, Application No. 201710391622.5.
CN Search Report dated Feb. 19, 2019, Application No. 201710391622.5.

* cited by examiner

Test piece preparation: assembling a prefabricating mold, mounting a fiber grating and a simulated wellbore, pouring cement mortar into the prefabricating mold for being solidified to form a test piece, and removing the prefabricating mold and curing the test piece.

Test piece mounting: mounting the test piece into a confining pressure chamber of a true triaxial hydraulic fracturing simulation device, connecting a liquid injection line to the true triaxial hydraulic fracturing simulation device, and connecting the fiber grating to a modem.

Hydraulic fracture width monitoring test: injecting liquid into the confining pressure chamber of the true triaxial hydraulic fracturing simulation device through the liquid injection line to apply three-direction confining pressures to the test piece, injecting liquid into the simulated wellbore, and starting the fiber grating and the modem to dynamically monitor the hydraulic fracture width in the test piece.

Test piece sectioning: ending the test when a hydraulic fracture inside the test piece reaches an outer surface of the test piece, relieving the three-direction confining pressures and disassembling the liquid injection line, removing the test piece from the true triaxial hydraulic fracturing simulation device, sectioning the test piece to observe a form of the fracture thereof.

EXPERIMENTAL METHOD FOR INDOOR REAL-TIME DYNAMIC MONITORING OF HYDRAULIC FRACTURE WIDTH

CROSS REFERENCE TO RELATED APPLICATIONS

This application claims priority to Chinese Invention Patent Application No. 201710391622.5 filed on May 27, 2017, which is incorporated herein by reference in its entirety.

TECHNICAL FIELD

The present disclosure relates to the technical field of hydraulic fracturing simulation tests, and particularly to an experimental method for indoor real-time dynamic monitoring of a hydraulic fracture width.

BACKGROUND ART

With the large-scale development of unconventional oil and gas reservoirs such as shale gas and coalbed methane, it is necessary to conduct basic researches on the hydraulic fracture extension mechanism under complex stress conditions and geological conditions, so as to provide a strong technical support and guarantee for on-site fracturing. At present, the actual form of the on-site hydraulic fracture cannot be directly observed. Facture information, such as fracture orientation, length, height, and scale, can only be obtained indirectly through geophysical testing methods such as logging, micro-deformation, and microseism, or by means of a true triaxial hydraulic fracturing simulation device in the laboratory, etc. The hydraulic fracture width cannot be monitored in real time, so it is difficult to accurately understand the hydraulic fracture extension mechanism at site and the mutual influences during the fracture propagation.

In view of this, the inventor develops an experimental method for indoor real-time dynamic monitoring of a hydraulic fracture width based on the production and design experiences in this and related fields, so as to solve the problems existing in the prior art.

SUMMARY OF THE INVENTION

An objective of the present disclosure is to provide an experimental method for indoor real-time dynamic monitoring of a hydraulic fracture width, which can realize real-time dynamic monitoring of the hydraulic fracture width under indoor laboratory conditions, thereby providing an important monitoring measure for the researches and demonstrations of the hydraulic fracturing theory.

To this end, the present disclosure proposes an experimental method for indoor real-time dynamic monitoring of a hydraulic fracture width, comprising the steps of:

a) test piece preparation: assembling a prefabricating mold and fixing a fiber grating within the prefabricating mold; next, mounting a simulated wellbore within the prefabricating mold, pouring agitated cement mortar into the prefabricating mold, and removing the prefabricating mold and curing a test piece after the cement mortar is solidified to form the test piece;

b) test piece mounting: mounting the test piece into a confining pressure chamber of a true triaxial hydraulic fracturing simulation device, connecting a liquid injection line to the true triaxial hydraulic fracturing simulation device, and connecting the fiber grating to a modem that is connected to a computer, so as to test integrality of the fiber grating and recordability of data;

c) hydraulic fracture width monitoring test: injecting liquid into the confining pressure chamber of the true triaxial hydraulic fracturing simulation device through the liquid injection line to apply three-direction confining pressures to the test piece, injecting liquid into the simulated wellbore, and starting the fiber grating and the modem to dynamically monitor the hydraulic fracture width in the test piece; and d) test piece sectioning: ending the test when a hydraulic fracture inside the test piece reaches an outer surface of the test piece, relieving the three-direction confining pressures and disassembling the liquid injection line, removing the test piece from the true triaxial hydraulic fracturing simulation device, and sectioning the test piece to observe a form of the fracture thereof.

In the experimental method for indoor real-time dynamic monitoring of a hydraulic fracture width as defined above, in the step a), the cement mortar is made of cement and quartz sand with a weight ratio of 1:1 and evenly agitated with water.

In the experimental method for indoor real-time dynamic monitoring of a hydraulic fracture width as defined above, a light source used by the modem is a laser broad-spectrum light source to ensure radiation stability of the light source.

In the experimental method for indoor real-time dynamic monitoring of a hydraulic fracture width as defined above, in the step a), an intermediate section of the fiber grating is perpendicular to the simulated wellbore.

In the experimental method for indoor real-time dynamic monitoring of a hydraulic fracture width as defined above, in the step a), two ends of the fiber grating run out of the prefabricating mold in such a manner that the two ends form curved arcs of greater than 90 degrees with the intermediate section, respectively.

In the experimental method for indoor real-time dynamic monitoring of a hydraulic fracture width as defined above, in the step c), during application of the three-direction confining pressures to the test piece in three directions, a minimum main stress is applied to the test piece in a length direction of an intermediate section of the fiber grating, while an intermediate main stress and a maximum main stress are applied to the test piece in the other two directions perpendicular to the intermediate section; during a fracturing test, a hydraulic fracture inside the test piece is extended in a direction perpendicular to the intermediate section of the fiber grating; wherein the minimum main stress, the intermediate main stress, and the maximum main stress are increased sequentially.

In the experimental method for indoor real-time dynamic monitoring of a hydraulic fracture width as defined above, in the step c), when the three-direction confining pressures are applied to the test piece, the pressures are applied synchronously in the three directions at the same rate of increasing the pressures; when a pressure in one of the directions reaches a set value, the pressure is kept constant, while pressures in the other two directions are continuously increased; and when each of the three-direction confining pressures reaches a set value, the pressures are maintained until the end of the test.

In the experimental method for indoor real-time dynamic monitoring of a hydraulic fracture width as defined above, wherein the prefabricating mold is formed by a base plate, a front end plate, a rear end plate, and two side plates in which a through hole is formed respectively; an iron wire placed in a horizontal direction is fixed between the two through holes, and an intermediate section of the fiber grating is fixed on the iron wire.

In the experimental method for indoor real-time dynamic monitoring of a hydraulic fracture width as defined above, wherein a front end of the simulated wellbore is fixed on the front end plate, a rear end of the simulated wellbore faces towards the rear end plate, and an intermediate section of the fiber grating is placed to be perpendicular to the simulated wellbore.

In the aforementioned experimental method for indoor real-time dynamic monitoring of a hydraulic fracture width as defined above, wherein a liquid inlet at the front end of the simulated wellbore is communicated with a liquid inflow hole in the front end plate, and a liquid outlet at the rear end of the simulated wellbore is provided with a prefabricated fracture.

As compared with the prior art, the present disclosure uses the fiber grating, the modem, and the true triaxial hydraulic fracturing simulation device, so that the real-time dynamic monitoring of the hydraulic fracture width can be performed in the course of the hydraulic fracturing simulation experiment, and a model of a hydraulic fracture extension mechanism is established based on the experimental result, thereby providing an important monitoring measure for researches and demonstrations of the fracturing theory, and the obtained research results can provide a strong technical support and guarantee for on-site fracturing.

The experimental method for indoor real-time dynamic monitoring of the hydraulic fracture width provided by the present disclosure has simple procedures and convenient operations, and meets the laboratory experimental requirements.

BRIEF DESCRIPTION OF THE DRAWINGS

The following drawings are only intended to schematically illustrate and explain the present disclosure, rather than limiting the scope of the present disclosure. In which.

REFERENCE NUMERALS OF THE MAIN ELEMENTS

1: prefabricating mold;
11: base plate;
12: front end plate;
121: liquid inflow hole;
13: rear end plate;
14: side plate;
15: iron wire;
2: fiber grating;
3: simulated wellbore;
31: prefabricated fracture;
4: test piece

DETAILED DESCRIPTION

The present disclosure proposes an experimental method for indoor real-time dynamic monitoring of a hydraulic fracture width, comprising the steps of: a) test piece preparation: assembling a prefabricating mold and fixing a fiber grating within the prefabricating mold; next, mounting a simulated wellbore within the prefabricating mold, pouring agitated cement mortar into the prefabricating mold, and removing the prefabricating mold and curing a test piece after the cement mortar is solidified to form the test piece; b) test piece mounting: mounting the test piece into a confining pressure chamber of a true triaxial hydraulic fracturing simulation device, connecting a liquid injection line to the true triaxial hydraulic fracturing simulation device, and connecting the fiber grating to a modem that is connected to a computer, so as to test integrality of the fiber grating and recordability of data; c) hydraulic fracture width monitoring test: injecting liquid into the confining pressure chamber of the true triaxial hydraulic fracturing simulation device through the liquid injection line to apply three-direction confining pressures to the test piece, injecting liquid into the simulated wellbore, and starting the fiber grating and the modem to dynamically monitor the hydraulic fracture width in the test piece; and d) test piece sectioning: ending the test when a hydraulic fracture inside the test piece reaches an outer surface of the test piece, relieving the three-direction confining pressures and disassembling the liquid injection line, removing the test piece from the true triaxial hydraulic fracturing simulation device, and sectioning the test piece to observe a form of the fracture thereof.

The experimental method for indoor real-time dynamic monitoring of the hydraulic fracture width according to the present disclosure can realize real-time dynamic monitoring of the hydraulic fracture width under indoor laboratory conditions, thereby providing an important monitoring measure for the researches and demonstrations of the hydraulic fracturing theory.

In order to more clearly understand the technical features, objective and effects of the present disclosure, hereinafter, the specific embodiments, structures, features and effects of the experimental method for indoor real-time dynamic monitoring of the hydraulic fracture width proposed by the present disclosure will be described in details with reference to the drawings and preferred embodiments. In addition, through the description of the specific embodiments, the technical means employed in the present disclosure to achieve the intended objective and the produced effects can be understood more deeply and specifically. However, the drawings are only used for reference and explanation rather than limiting the present disclosure.

Figure 1:
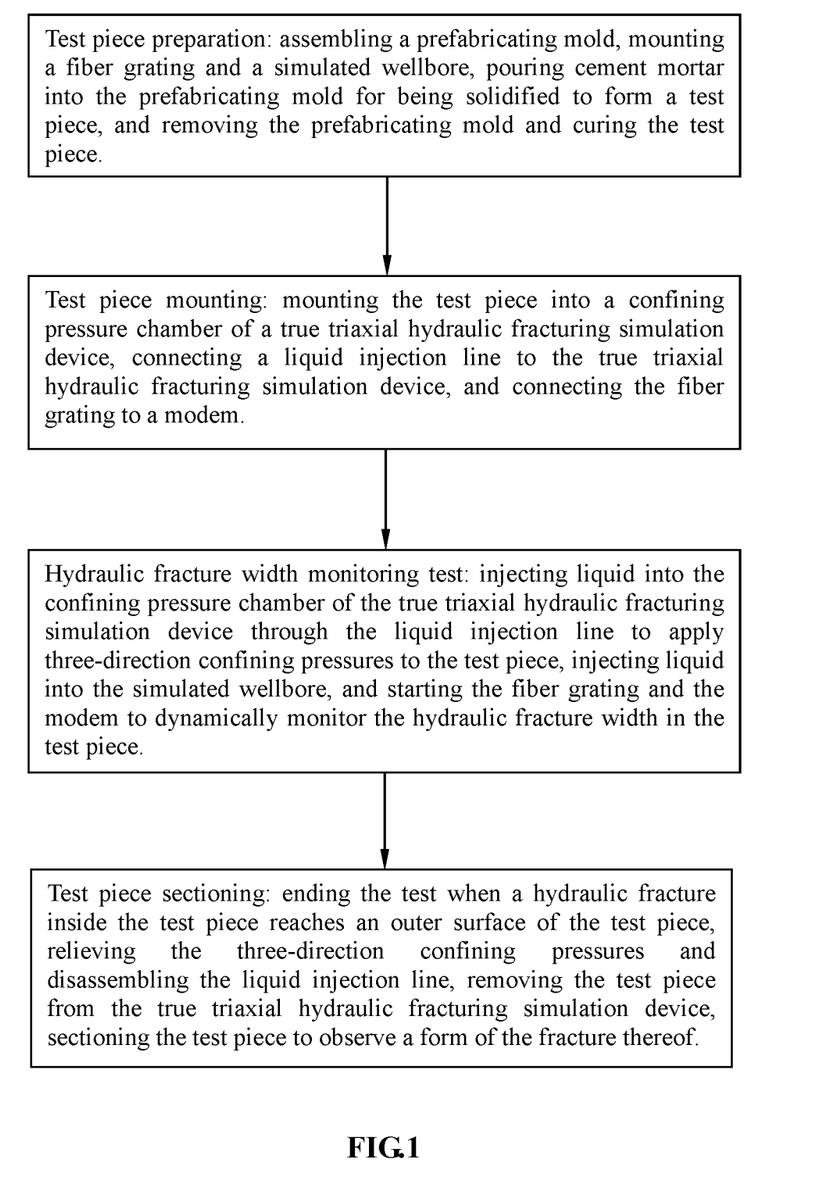
FIG. 1 is a schematic diagram of working steps for indoor real-time dynamic monitoring of a hydraulic fracture width of the present disclosure.
Figure 2:
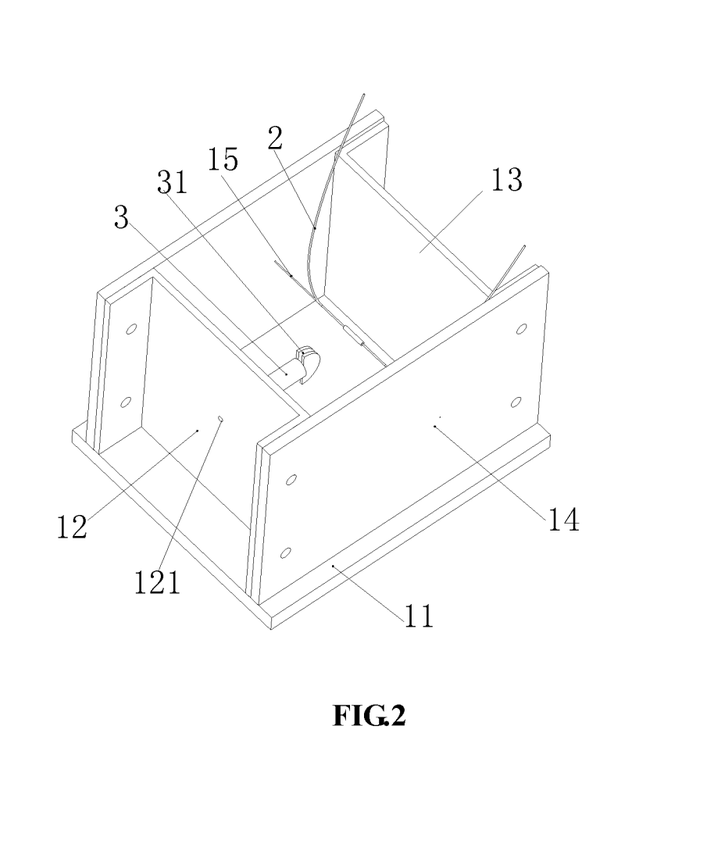
FIG. 2 is a schematic diagram of a connection between a prefabricating mold and a fiber grating in the present disclosure.
Figure 3:
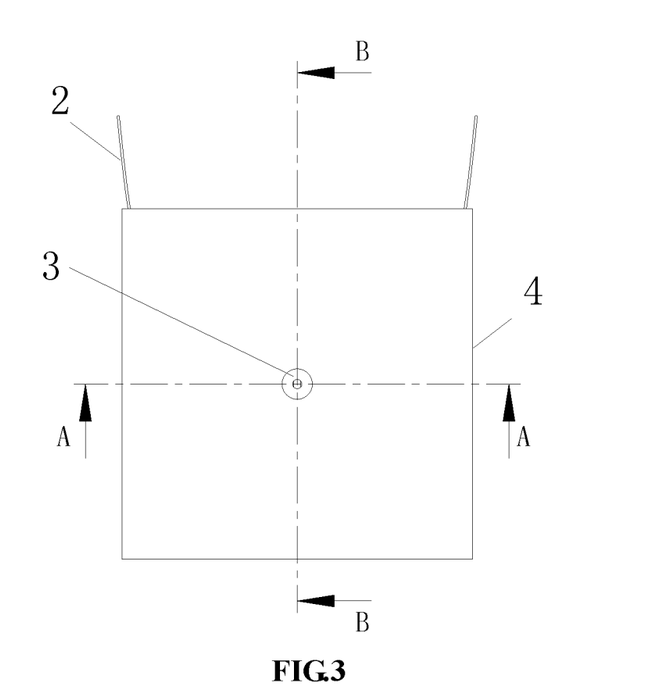
FIG. 3 is a front view of a test piece according to the present disclosure.
Figure 4:
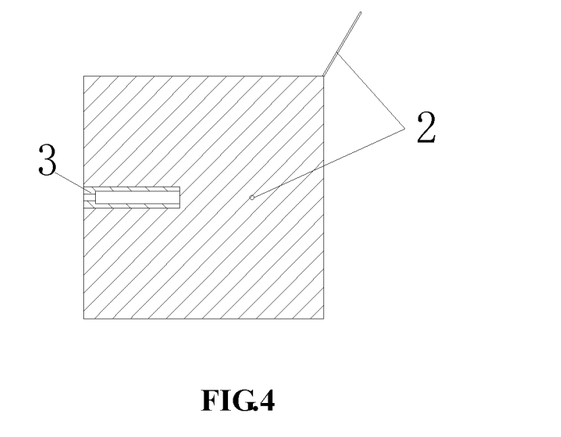
FIG. 4 is a sectional view taken along line A-A in FIG. 3.
Figure 5:
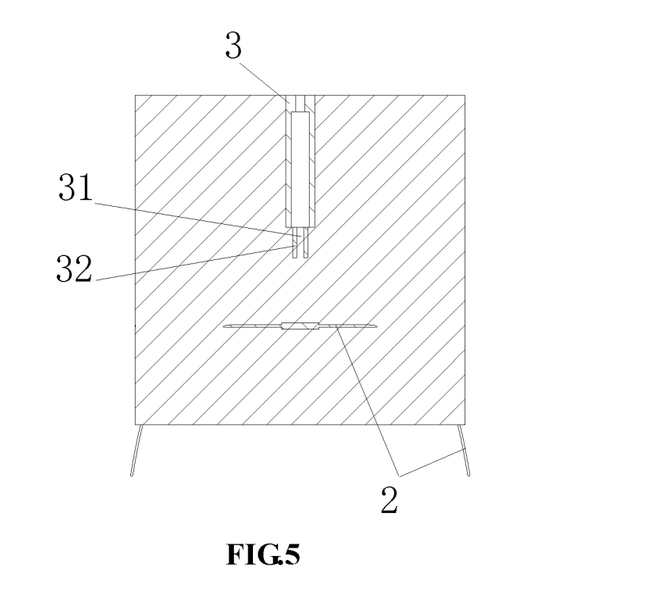
FIG. 5 is a sectional view taken along line B-B in FIG. 3.

FIG. 1 is a schematic diagram of working steps for indoor real-time dynamic monitoring of a hydraulic fracture width according to the present disclosure. FIG. 2 is a schematic diagram of a connection between a prefabricating mold and a fiber grating in the present disclosure. FIG. 3 is a front view of a test piece in the present disclosure. FIG. 4 is a sectional view taken along line A-A in FIG. 3. FIG. 5 is a sectional view taken along line B-B in FIG. 3.

As illustrated in FIG. 1, the present disclosure proposes an experimental method for indoor real-time dynamic monitoring of a hydraulic fracture width, comprising the steps of:

a) test piece preparation: assembling a prefabricating mold and fixing a fiber grating within the prefabricating mold; next, mounting a simulated wellbore within the prefabricating mold, pouring agitated cement mortar into the prefabricating mold, and removing the prefabricating mold and curing a test piece after the cement mortar is solidified to form the test piece;

b) test piece mounting: mounting the test piece into a confining pressure chamber of a true triaxial hydraulic fracturing simulation device, connecting a liquid injection line to the true triaxial hydraulic fracturing simulation device, and connecting the fiber grating to a modem that is connected to a computer, so as to test integrity of the fiber grating and recordability of data; wherein the true triaxial hydraulic fracturing simulation devices, the modem, and the computer are all the prior arts, and their constituent structures and specific working principles will not be described;

c) hydraulic fracture width monitoring test: injecting liquid into the confining pressure chamber of the true triaxial hydraulic fracturing simulation device through the liquid injection line to apply three-direction confining pressures to the test piece, injecting liquid into the simulated wellbore, and starting the fiber grating and the modem to dynamically monitor the hydraulic fracture width in the test piece; and d) test piece sectioning: ending the test when a hydraulic fracture inside the test piece reaches an outer surface of the test piece, relieving the three-direction confining pressures and disassembling the liquid injection line, removing the test piece from the true triaxial hydraulic fracturing simulation device, and sectioning the test piece to observe a form of the fracture thereof.

In practical applications, the true triaxial hydraulic fracturing simulation device is preferably a "triaxial mechanical property test device for large rock" disclosed in Chinese publication No. CN203869957U, so as to carry out a three-direction confining pressure test on the test piece; its specific use method is a known art, and will not be described herein; the dimensions of the test piece are preferably of 300 mm (length)×300 mm (width)×300 mm (height), but the practical operations are not limited thereto; during the experiment, the liquid to be injected is preferably a 2% red guar gum solution serving as a fracturing fluid, and a liquid injection rate is 8 mL/min.

Preferably, in the step a), the cement mortar is made of cement and quartz sand with a weight ratio of 1:1 and evenly agitated with water. Specifically, cement and quartz sand with a weight ratio of 1:1 are mixed and then evenly agitated with water, and the agitated cement mortar is poured into the prefabricating mold; when the cement mortar reaches the top of the prefabricating mold, a pre-test piece is troweled with a trowel; preferably, the prefabricating mold is removed after 1 to 2 days from the solidification of the cement mortar, and the test piece is put in a cool and ventilated place for 28 days while being watered continuously, so as to better meet the design strength.

A light source used by the modem is a laser broad-spectrum light source to ensure a radiation stability of the light source. In practical work, the modem emits a laser broad-spectrum light wave, so as to test integrality of the fiber grating by monitoring whether the fiber grating returns the light wave, and test recordability of data by testing whether the light wave is within a monitoring range of the modem. The specific use method of the modem is the prior art and will not be described herein. Preferably, the modem is a MOI Si155 type modem.

In the step a), an intermediate section (i.e., the grating area) of the fiber grating 2 is perpendicular to the simulated wellbore 3 (referring to FIG. 2).

Further, in the step a), two ends of the fiber grating run out of the prefabricating mold in such a manner that the two ends form curved arcs of greater than 90 degrees with the intermediate section of the fiber grating, respectively.

In the step c), during application of the three-direction confining pressures to the test piece in three directions, a minimum main stress is applied to the test piece in a length direction of the intermediate section of the fiber grating, while an intermediate main stress and a maximum main stress are applied to the test piece in the other two directions perpendicular to the intermediate section; during a fracturing test, a hydraulic fracture inside the test piece is extended in a direction perpendicular to the intermediate section of the fiber grating; wherein the minimum main stress, the intermediate main stress, and the maximum main stress are increased sequentially. As illustrated in FIG. 2, the directions of the three-direction confining pressures are preferably a width direction, a length direction and a height direction of the prefabricated member/test piece. Among the three pressures, preferably, the pressure applied in the length direction of the intermediate section of the fiber grating is the minimum main stress, while the other two pressures are the intermediate main stress and the maximum main stress, respectively, and the values of the three pressures are increased sequentially.

Further, in the step c), when the three-direction confining pressures are applied to the test piece, the pressures (stresses) are applied synchronously in the three directions at the same rate of increasing the pressures; when a pressure in one of the directions reaches a set value, it is kept constant, and pressures in the other two directions are continuously increased; and when each of the three-direction confining pressures reaches a set value, the pressures are maintained until the end of the test.

For example, in the illustrated structure, the three-direction confining pressures to be applied on the test piece are 9 MPa, 15 MPa, and 17 MPa, respectively, and the specific process is as follows: the pressures are simultaneously applied at the same rate of increasing pressure from zero in three directions; when the pressure applied in the length direction of the intermediate section of the fiber grating 4 is 9 MPa, it is kept stable; the pressure in the direction of the simulated wellbore is continuously increased to 15 MPa and then kept stable; the pressure in the last direction, i.e., the height direction of the test piece, is continuously increased to 17 MPa; when the confining pressures in the three directions reach 9 MPa, 15 MPa and 17 MPa respectively, the pressures are kept stable until the end of the experiment.

Referring to FIG. 2, the prefabricating mold 1 is formed by a base plate 11, a front end plate 12, a rear end plate 13, and two side plates 14 in which a through hole (not illustrated) is formed respectively; an iron wire 15 placed in a horizontal direction is fixed between the two through holes, and an intermediate section of the fiber grating 2 is fixed on the iron wire 15, so that the iron wire 15 and the intermediate section of the fiber grating 2 are arranged in the width direction of the prefabricating mold. Upon fixing the fiber grating 2, it is necessary to avoid excessive stretching or bending, thereby preventing the failure of the fiber grating 2 due to the excessive stretching or bending.

Preferably, the front end of the simulated wellbore 3 is fixed on the front end plate 12 via bolted connection and so on, the rear end of the simulated wellbore 3 faces towards the rear end plate 13, and the intermediate section of the fiber grating 2 is placed to be perpendicular to the simulated wellbore 3. That is, in the illustrated structure, the simulated wellbore 3 is placed in the length direction of the prefabricating mold 1, while the fiber grating 2 is placed in the width direction of the prefabricating mold 1 so as to be orthogonal and perpendicular to the prefabricating mold 1.

A liquid inlet in the front end of the simulated wellbore 3 is communicated with a liquid inflow hole 121 in the front end plate 12, and a liquid outlet at the rear end of the simulated wellbore 3 is provided with a prefabricated fracture 31 for guiding an orientation of the hydraulic fracture. In practical use, as illustrated in FIGS. 3 to 5, preferably two semicircular rigid plastic sheets 32 are fixed at the liquid outlet of the simulated wellbore 3, so as to form a prefabricated fracture. Specifically, before the cement mortar is poured into the prefabricating mold, the two semicircular rigid plastic sheets may be directly fixed at the liquid outlet of the rear end of the simulated wellbore 3 via sewing and so on, so that the plastic sheets 32 are placed in the axial direction of the simulated wellbore; after the cement mortar is poured and solidified, a gap communicated with the simulated wellbore 3 is formed between the two semicircular rigid plastic sheets, thereby prefabricating the fracture.

The experimental method for indoor real-time dynamic monitoring of the hydraulic fracture width provided by the present disclosure has simple procedures and convenient operations; by using the fiber grating, the modem and the true triaxial hydraulic fracturing simulation device, real-time dynamic monitoring of the hydraulic fracture width can be performed in the course of the hydraulic fracturing simulation experiment, and a model of a hydraulic fracture extension mechanism can be established based on the experimental result, thereby providing an important monitoring measure for researches and demonstrations of the fracturing theory, and the obtained research results can provide a strong technical support and guarantee for on-site fracturing.

The above description is just illustrative of exemplary embodiments of the present disclosure, rather than limiting to the scope of the present disclosure. Any equivalent changes or amendments made by a person skilled in the art without deviating from the conception and principle of the present disclosure shall fall within the protection scope of the present disclosure.

The invention claimed is:

1. An experimental method for indoor real-time dynamic monitoring of a hydraulic fracture width, comprising the steps of:
   a) test piece preparation: assembling a prefabricating mold and fixing a fiber grating within the prefabricating mold; next, mounting a simulated wellbore within the prefabricating mold, pouring agitated cement mortar into the prefabricating mold, and removing the prefabricating mold and curing a test piece after the cement mortar is solidified to form the test piece;
   b) test piece mounting: mounting the test piece into a confining pressure chamber of a true triaxial hydraulic fracturing simulation device, connecting a liquid injection line to the true triaxial hydraulic fracturing simulation device, and connecting the fiber grating to a modem that is connected to a computer, so as to test integrity of the fiber grating and recordability of data;
   c) hydraulic fracture width monitoring test: injecting liquid into the confining pressure chamber of the true triaxial hydraulic fracturing simulation device through the liquid injection line to apply three-direction confining pressures to the test piece, injecting liquid into the simulated wellbore, and starting the fiber grating and the modem to dynamically monitor the hydraulic fracture width in the test piece; during application of the three-direction confining pressures to the test piece in three-directions, a minimum main stress is applied to the test piece in a length direction of an intermediate section of the fiber grating, while an intermediate main stress and a maximum main stress are applied to the test piece in two other directions perpendicular to the intermediate section; during a fracturing test, a hydraulic fracture inside the test piece is extended in a direction perpendicular to the intermediate section of the fiber grating; wherein the minimum main stress, the intermediate main stress, and the maximum main stress are increased sequentially; and
   d) test piece sectioning: ending the test when a hydraulic fracture inside the test piece reaches an outer surface of the test piece, relieving the three-direction confining pressures and disassembling the liquid injection line, removing the test piece from the true triaxial hydraulic fracturing simulation device, and sectioning the test piece to observe a form of the fracture thereof.

2. The experimental method for indoor real-time dynamic monitoring of a hydraulic fracture width according to claim 1, wherein in the step a), the cement mortar is made of cement and quartz sand with a weight ratio of 1:1 and evenly agitated with water.

3. The experimental method for indoor real-time dynamic monitoring of a hydraulic fracture width according to claim 1, wherein a light source used by the modem is a laser broad-spectrum light source to ensure radiation stability of the light source.

4. The experimental method for indoor real-time dynamic monitoring of a hydraulic fracture width according to claim 1, wherein in the step a), an intermediate section of the fiber grating is perpendicular to the simulated wellbore.

5. The experimental method for indoor real-time dynamic monitoring of a hydraulic fracture width according to claim 4, wherein in the step a), two ends of the fiber grating run out of the prefabricating mold in such a manner that the two ends form curved arcs of greater than 90 degrees with the intermediate section, respectively.

6. The experimental method for indoor real-time dynamic monitoring of a hydraulic fracture width according to claim 5, wherein in the step c), when the three-direction confining pressures are applied to the test piece, the pressures are applied synchronously in the three directions at a same rate of increasing the pressures; when a pressure in one of the directions reaches a set value, the pressure is kept constant, while pressures in the other two directions are continuously increased; and when each of the three-direction confining pressures reaches a set value, the pressures are maintained until an end of the test.

7. The experimental method for indoor real-time dynamic monitoring of a hydraulic fracture width according to claim 1, wherein the prefabricating mold is formed by a base plate, a front end plate, a rear end plate, and two side plates in which a through hole is formed respectively; an iron wire placed in a horizontal direction is fixed between the two through holes, and an intermediate section of the fiber grating is fixed on the iron wire.

8. The experimental method for indoor real-time dynamic monitoring of a hydraulic fracture width according to claim 7, wherein a front end of the simulated wellbore is fixed on the front end plate, a rear end of the simulated wellbore faces towards the rear end plate, and the intermediate section of the fiber grating is placed to be perpendicular to the simulated wellbore.

9. The experimental method for indoor real-time dynamic monitoring of a hydraulic fracture width according to claim 8, wherein a liquid inlet at the front end of the simulated wellbore is communicated with a liquid inflow hole in the front end plate, and a liquid outlet at the rear end of the simulated wellbore is provided with a prefabricated fracture.

10. The experimental method for indoor real-time dynamic monitoring of a hydraulic fracture width according to claim 5, wherein the prefabricating mold is formed by a base plate, a front end plate, a rear end plate, and two side plates in which a through hole is formed respectively; an iron wire placed in a horizontal direction is fixed between the two through holes; and an intermediate section of the fiber grating is fixed on the iron wire.

11. The experimental method for indoor real-time dynamic monitoring of a hydraulic fracture width according to claim 10, wherein a front end of the simulated wellbore is fixed on the front end plate, a rear end of the simulated wellbore faces towards the rear end plate, and the intermediate section of the fiber grating is placed to be perpendicular to the simulated wellbore.

12. The experimental method for indoor real-time dynamic monitoring of a hydraulic fracture width according to claim 11, wherein a liquid inlet at the front end of the simulated wellbore is communicated with a liquid inflow hole in the front end plate, and a liquid outlet at the rear end of the simulated wellbore is provided with a prefabricated fracture.

* * * * *